United States Patent [19]

Bagg et al.

[11] 3,965,722

[45] June 29, 1976

[54] APPARATUS FOR THE MEASUREMENT OF VISCOSITY

[75] Inventors: Greville Euan Gordon Bagg, Waltham Abbey; Robert Ian Cracknell, Hoddesdon, both of England

[73] Assignee: National Research Development Corporation, London, England

[22] Filed: May 3, 1974

[21] Appl. No.: 466,892

Related U.S. Application Data

[63] Continuation-in-part of Ser. No. 279,770, Aug. 11, 1972, abandoned.

[52] U.S. Cl. .................................................. 73/59
[51] Int. Cl.² ........................................ G01N 11/16
[58] Field of Search ...................... 73/59, 54, 17 R

[56] References Cited
UNITED STATES PATENTS

| | | | |
|---|---|---|---|
| 1,942,920 | 1/1934 | Fawkes | 73/59 |
| 2,485,424 | 10/1949 | Weisz | 73/59 |
| 2,696,735 | 12/1954 | Woodward | 73/59 |
| 2,708,361 | 5/1955 | Boyle et al. | 73/59 |
| 2,759,355 | 8/1956 | Boyle et al. | 73/59 |
| 3,090,223 | 5/1963 | Juffa et al. | 73/59 |

*Primary Examiner*—James J. Gill
*Assistant Examiner*—Joseph W. Roskos
*Attorney, Agent, or Firm*—Cushman, Darby & Cushman

[57] ABSTRACT

An apparatus for detecting a change in viscosity of a material, such as a molten plastics material, the change being from a highly fluid state to a high viscosity "set" state, comprising a probe, the combination comprising a motor such as an ironless motor for rotating said probe in a sample of the material and an operational amplifier having a feedback loop electrically connected to said motor, and means for measuring a parameter of the said combination, which parameter varies in accordance with the logarithm of the viscosity of said sample of material.

6 Claims, 5 Drawing Figures

APPARATUS FOR THE MEASUREMENT OF VISCOSITY

This invention relates to apparatus for the measurement of viscosity of a viscous material such as, for example, a molten plastics material, and to use of the apparatus to control the processing of such material by conventional processing apparatus, and is a continuation-in-part of application Ser. No. 279,770 filed on Aug. 11, 1972, now abandoned.

Many moulding processes involve a stage of applying pressure to a material to be moulded when the material has a viscosity within a specific critical range. This stage is particularly critical when moulding thermo-setting plastics resins which, typically, pass from a highly fluid state, through a useful working viscosity range to an unworkably high viscosity "set" state in a few minutes and, sometimes, in a few seconds. For example, the accompanying FIG. 1 shows the changes in resin viscosity which occur during the curing cycle of a short staple carbon fibre reinforced epoxy resin cured at 170°C with a fluoroborate catalyst (DX 210/BF$_3$ 400 products of Shell Chemicals Ltd). The viscosity of this resin at 25°C is 15 poise, see the publication "Epikote Resins Epikote DX210" published by Shell Chemicals Ltd in December 1970. Starting with cold resin at Point A, the viscosity decreases as the resin is heated (B) until the onset of polymerisation at point C when a rapid increase in viscosity occurs ending with gelation at point E and effectively infinite viscosity. The accompanying FIG. 2 illustrates more clearly the viscosity changes just before and after the onset of polymerisation. The accompanying FIG. 3 illustrates the viscosity changes just before and after polymerisation in the curing cycle of a polyester resin at 100°C, in which the time betweeen onset of polymerisation C and effectively infinite viscosity E is only 10 seconds compared with 42 seconds for the epoxy resin.

During the moulding process, the resin viscosity generally varies from a value of a few poise to effectively infinite viscosity in the "set" state. See, for example, CIBA Publication No. C395 published in February 1969 in which the viscosities of various types of resin are stated to be between 10 and 400 poise, (usually between 10 and 50 poise), at 21°C, and between ½ and 4 poise at 60°C, before chemical reaction causes viscosity to increase until the resin hardens or "sets." Such a change of viscosity is of at least three orders of magnitude. It is an object of the present invention to provide apparatus capable of measuring changes of viscosity over such a range or within such short periods of time.

When forming resin-bound composites, such as laminates and fibre reinforced resin, if pressure is applied when the resin is at too low a viscosity the resin will flow out of the composite leaving it resin starved. If however, the resin viscosity is too high when the pressure is applied, there will be insufficient resin flow to consolidate the composite and fill the voids. For optimum physical properties in the composite, pressure must be applied when the resin is just starting to polymerise and before complete polymerisation, eg within the 10 second period between points C and E in FIG. 3. The viscosity may also be critical when extruding or injection moulding thermoplastic materials.

Previously such processes have been controlled by measurement of electrical parameters, such as dielectric properties or resistance or have relied on operator skill and judgment in observing the state of the material.

Electrical methods normally require a complex electrical probe and/or interpretation equipment and are therefore expensive. Such methods also require a relatively large sample and it is often necessary to take measurements on the bulk of the material. This may result in difficulty in removing a large probe from the product. In addition, electrical methods may be sensitive to the presence of gas bubbles or voids in the resin and are difficult to use for measuring the viscosity of an electrically conducting or semi-conducting material, such as a plastics material filled with carbon fibres.

Methods depending on operator skill do not yield sufficiently reproducible results for many purposes and are far from ideal for mass production.

It is another object of the invention to provide apparatus which can be used to control such processes more accurately.

According to the invention, apparatus capable of detecting a change in the viscosity of a material, said change being from a highly fluid state to a high viscosity "set" state, consists of a probe, the combination comprising a motor which can rotate said probe in a sample of the material and an operational amplifier having a feedback loop in which said motor is arranged, and means to measure a parameter of the said combination, the apparatus being arranged so that said parameter varies in accordance with the logarithm of the viscosity of said sample of material. Preferably said parameter varies in direct proportion to said logarithm of the viscosity over a substantial part of the range of the parameter.

Preferably the motor is an ironless motor because such a motor is intrinsically capable of operating over a wide range of probe speeds and therefore of viscosities without the use of gearing, without a change of probe, and without a change of range on the means to measure the parameter of the motor. An ironless motor is stable at low speeds, and will not be damaged under stalled conditions when a resin "sets." Use of such a motor allows the provision of apparatus which is sensitive even at low viscosity and which can give repeatable results under identical conditions. Such conditions are not met by the use, for example, of Ashunt-wound D.C. motor, which can also furnish information over a wide range of speeds.

The apparatus is conveniently provided with a constant voltage source which can drive the ironless motor, and with means to measure the current drawn by the motor, whereby in use the current drawn varies in accordance with the logarithm of the viscosity of said sample of material. Preferably the operational amplifier is arranged as an active filter/integrator. In the arrangement the current drawn varies in direct proportion to said logarithm over a substantial part of the current range, ie the relationship between current and viscosity has a "logarithmic nature," to use conventional electronics terminology.

The feedback loop may include a current meter, such as a milliammeter, and a variable resistor in series whereby, with the motor running, the current meter may be set to zero by variation of the variable resistor and may be set to full scale deflection by preventing rotation of the probe, eg by holding it with the fingers.

Although it will generally be more convenient to provide a constant voltage source, alternatively the motor may be supplied by a constant current source whereby the voltage applied to the motor is a function of the speed of rotation of the probe.

Optionally, the means for measuring the electrical parameter may be arranged to provide a visible and/or audible signal when the retarding force reaches a predetermined value and the processing means may be controlled manually. Alternatively, or additionally, the means for measuring the parameter may control servomechanical means arranged to control processing means for the viscous material. For example, the servomechanical means may be arranged to actuate an increase in the pressure applied by a conventional plastics compression press to a material such as a reinforced plastics composite.

The substantially logarithmic relation between the measured parameter and the viscosity of the material allows a single instrument to measure the wide range of viscosity which occurs in a typical moulding cycle of a thermosetting resin. The facilities for setting the current meter to zero and full scale deflection means that no internal calibration is required.

The probe may be any device which, when attached to the motor, is rotatable in the material to be moulded without causing substantial displacement of said material. It may be in the shape of a ball, cylinder or a flat disc attached to a rod perpendicular to the plane of the disc. Alternatively, especially when the final viscosity of the material is high, the probe may be a simple rod of glass or other cheap material which may be discarded after each moulding cycle. The probe should preferably have a low thermal conductivity to avoid any undesirable heating or cooling of the sample. In another form the probe may be of such shape as to act as a stirrer for the viscous material, eg paddle shaped.

The probe may be inserted into a sample which is part of the bulk of the material to be moulded or may be inserted into a separate sample of the material which has had substantially the same treatment as the bulk since it was removed therefrom, either before or after commencing the moulding operation. Where a separate sample is used, it may conveniently be obtained by applying pressure to the bulk of the material to cause a small sample, or flash, to flow into a small secondary chamber adjacent to the mould into which the probe may be inserted.

Since the absolute viscosity is not required, the probe need not be made with high precision, thereby offering a considerable economy over previous techniques using high precision probes and enabling the probe to be discarded after each run. This fact offers particular advantages when moulding thermosetting resins since the probe may be left in the resin until the resin has completely set rather than being withdrawn for re-use just before this stage. It is also found that the presence of gas bubbles in the sample whose viscosity is being monitored does not seriously affect the usefulness and reproducibility of the measurements especially when, as with thermosetting resins, the change in viscosity of the material during the moulding cycle is large compared with the change due to the presence of bubbles. This is in marked contrast to the electrical methods used for monitoring viscosity which tend to be sensitive to the presence of even small bubbles since the magnitude of the changes in electrical properties observed with changing viscosity is normally much smaller than the magnitude of changes due to the presence of, for example, air. Similarly the depth of immersion of the probe is not critical.

The apparatus of the invention is particularly useful when used to control the manufacture of reinforced plastics composites from aligned short staple prepregs. Such prepregs have low natural packing and a large volume of air must be expelled from the sample to produce a composite with a high fibre loading. Initial quantities of air are expelled easily but removal of the last traces of air and of the excess resin requires very careful control; this stage is most important if optimum properties are to be obtained.

The apparatus of the invention provides a continuous analogue output related to viscosity, and may therefore be used to study the curing cycle of a moulding material.

Whilst the invention particularly relates to moulding plastics materials, especially thermosetting plastics, the apparatus is also applicable to the moulding of other materials, such as metals, when the viscosity is critical, and may also be used to monitor the viscosity of materials such as slurries. The invention, particularly when using a probe of such a shape as to stir the viscous material, may also be used for a process such as a chemical reaction in a liquid medium, the viscosity of the liquid changing when, for example, precipitation occurs.

The invention will now be further described by way of example only with reference to the accompanying drawings in which:-

FIG. 5 illustrates the principle of the electrical measuring circuit;

Figure 4:
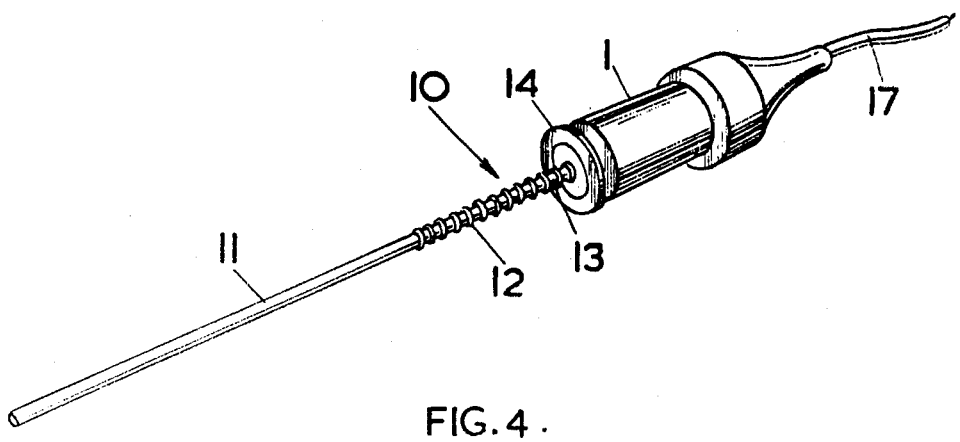
FIG. 4 illustrates a probe and a motor according to the invention.

In FIG. 4, a probe indicated generally by reference 10 comprises a glass rod 11 connected by a flexible spring coupling 12 to the boss 13 of an aluminium disc 14. The disc 14 is press-fitted and sealed to the shaft 15 of an ironless motor 1, and protects the motor bearings from atmospheric pollution and splashes from the material the viscosity of which is being measured. The motor 1 is connected by an electrical cable 17 to a circuit described below. The motor may for example be a Maxon dc motor Type 2116.290.112 and may be protected by an air-purged jacket if necessary. In another form the spring coupling 12 may be replaced by a rubber tube.

FIG. 5 illustrates the principle of operation when the ironless motor is supplied from a constant voltage source and the current drawn is measured. In the FIG. the motor 1 is arranged in the feedback loop of a differential operational amplifier 6; the amplifier is also wired as an active filter/integrator. One input of amplifier 6 is connected to a speed setting potentiometer at 5 and the output of amplifier 6 is connected through a milliammeter 4 to a resistor 2. The output is also connected to the first input of a differential amplifier 7, the second input of which is connected to a trip level setting potentiometer at 3. The output of amplifier 7 controls a relay 8 having contacts 8(1) and 8(2).

In operation, the voltage picked off potentiometer 5 is a reference voltage set to correspond to the rotational speed of motor 1 at which the circuit is required to trip. This speed is related to the viscosity of the sample in which glass rod 11 is immersed. The reference voltage is compared by amplifier 6 with the voltage across resistor 2 due to current drawn by the motor 1 and the meter 4 displays any change in current drawn by the motor 1 when loaded.

Amplifier 7 is a trip level sensing amplifier arranged to act as a relay driver; the relay 8 controls contacts which can operate either audible or visible signal means, and/or servomechanical means to control the processing means for the viscous material. A separate "set zero" control 9 (not shown) is provided to back-off the current drawn by the unloaded motor; the voltage due to such current is arranged to appear as a common mode signal to amplifier 7 and is rejected.

Figure 6:
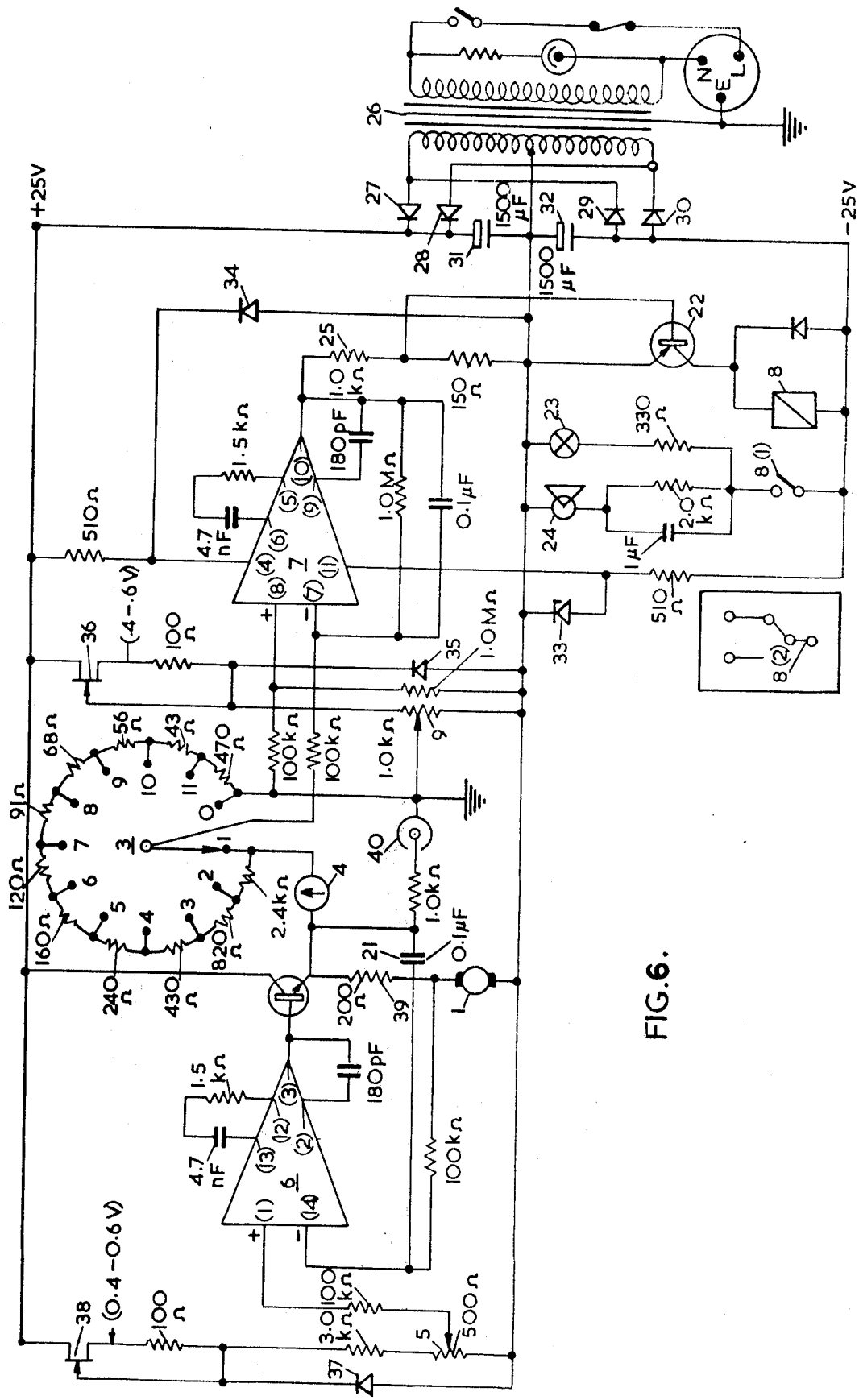
FIG. 6 illustrates a suitable electrical circuit to which the probe and motor may be connected.

A suitable circuit is shown in detail in FIG. 6 in which the motor 1 is connected in the feedback loop of an operational amplifier 6 such as a type Ser. No. 72709 DN. The motor drive voltage derived from set speed resistor 5 is connected to the non-inverting input of amplifier 6 and the amplifier output is connected to a transistor 20 such as a type BFT39; the voltage on the emitter of this transistor increases as the load on motor 1 increases. In order to reduce commutation ripple and "cogging" effects when the motor 1 is operating at slow speeds, a capacitor 21 is incorporated across the feedback loop so that the stage acts as an active low pass filter/integrator.

A 12-way break-before-make switch 3 (the trip level potentiometer) can be set to a resistance which determines a preset trip level voltage. The motor offset voltage appears as a common mode signal to the amplifier 7 and is rejected, the trip signal only being sensed by amplifier 7. The output of amplifier 7 drives through a transistor 22, which may be a type BF T79, a relay 8 the contact 8(1) of which controls a trip indicator lamp 23 and an annunciator 24 which are actuated when the voltage level preset on switch 3 is reached. Relay 8 also controls contacts 8(2) which may actuate servomechanical means (not shown). If the current gain spread of transistor 22 is wide, the trip calibration resistor 25 may be altered in value.

The circuit is supplied from a floating 25/0/25 volt supply comprising a mains transformer 26, four bridge rectifier diodes 27, 28, 29, 30, such as type 1S B05, and two capacitors 31, 32. Zener diodes 33 and 34 are voltage stabilising diodes. The zero control comprises a variable resistor 9 connected to the supply through a zener diode 35 such as a type BZY88 which is constant current sourced by a field effect transistor 36 such as a type 2N 3819. The sensitivity or motor speed control voltage is derived from a variable resistor 5 supplied through a similar arrangement of a Zener diode 37 and a field effect transistor 38. When the motor 1 is running in an unloaded condition, there is an offset voltage and variable resistor 9 allows the metering and trip circuits to be backed off. The motor 1 is supplied with current through a resistor 39.

The relay 8, trip indicator 23 and annunciator 24 are placed in the negative supply line to balance the total load on the supply rails.

In operation, the circuit is switched on and allowed to run with the speed setting high. The motor 1 is then stalled by gently holding the glass rod 11 and the resistor 5 is altered to give a full scale reading on the meter 4. The zero is checked and adjusted if necessary by altering resistor 9. The circuit will then operate the relay 8 when the retarding force on the glass rod 11 and therefore on motor 1 corresponds to the value set on switch 3.

The output of the circuit may be recorded on a high impedance chart recorder (not shown), which can be connected into the circuit at a monitor position 40, and a relative viscosity profile may be logged.

Figure 7:
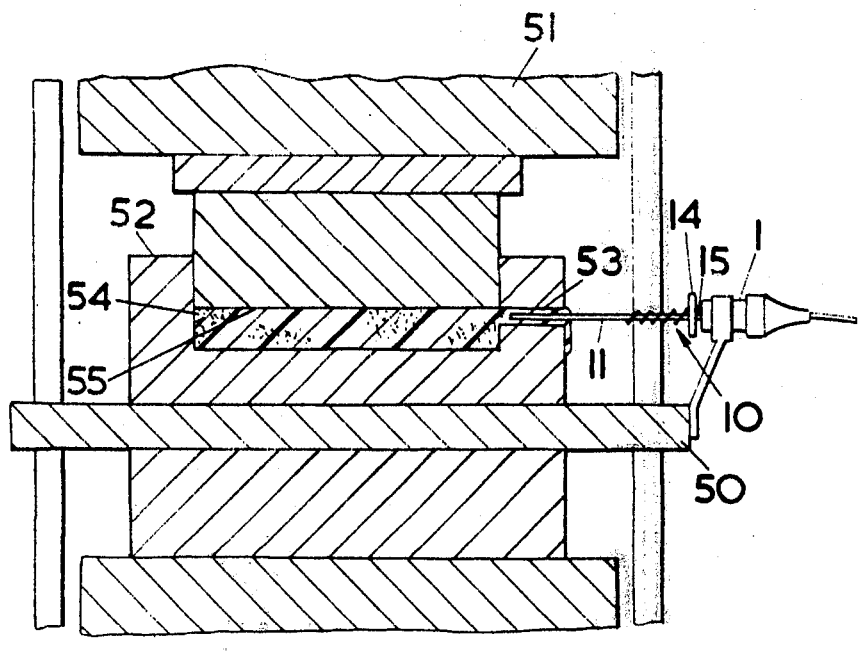
FIG. 7 illustrates a compression moulding press controlled according to the invention.

In FIG. 7 a probe 10 is arranged with the motor 1 clamped to the lower platen 50 of a bottom stroking compression moulding press. Between the upper and lower platens 51 and 50 is a mould 52 containing in a first chamber 55 a plastics laminate 54. The mould 52 has a spillway or second chamber 53 in which the glass rod 11 of probe 10 can be inserted.

In operation the mould 52 is loaded with prepregs of resin impregnated short staple carbon fibre having a high void content and the mould is then placed between heated press platens 50, 51 and allowed to heat up.

When the resin has become sufficiently fluid, slight pressure is applied to the mould causing a small sample of resin to flow from the main chamber 55 into the spillway 53 adjacent to it.

The probe 10, clean and grease-free, is inserted into the sample of resin, the zero control 4 is adjusted to give a zero reading and the sensitivity control 9 is adjusted to give a standard, preselected fullscale reading at motor stall (simulated by manually holding the probe stationary) which corresponds to complete gelation of the resin. The equipment therefore measures the effective changes in viscosity of the resin from the onset of polymerisation to complete gelation in arbitrary units and does not require calibration to give specific values.

Figure 1:
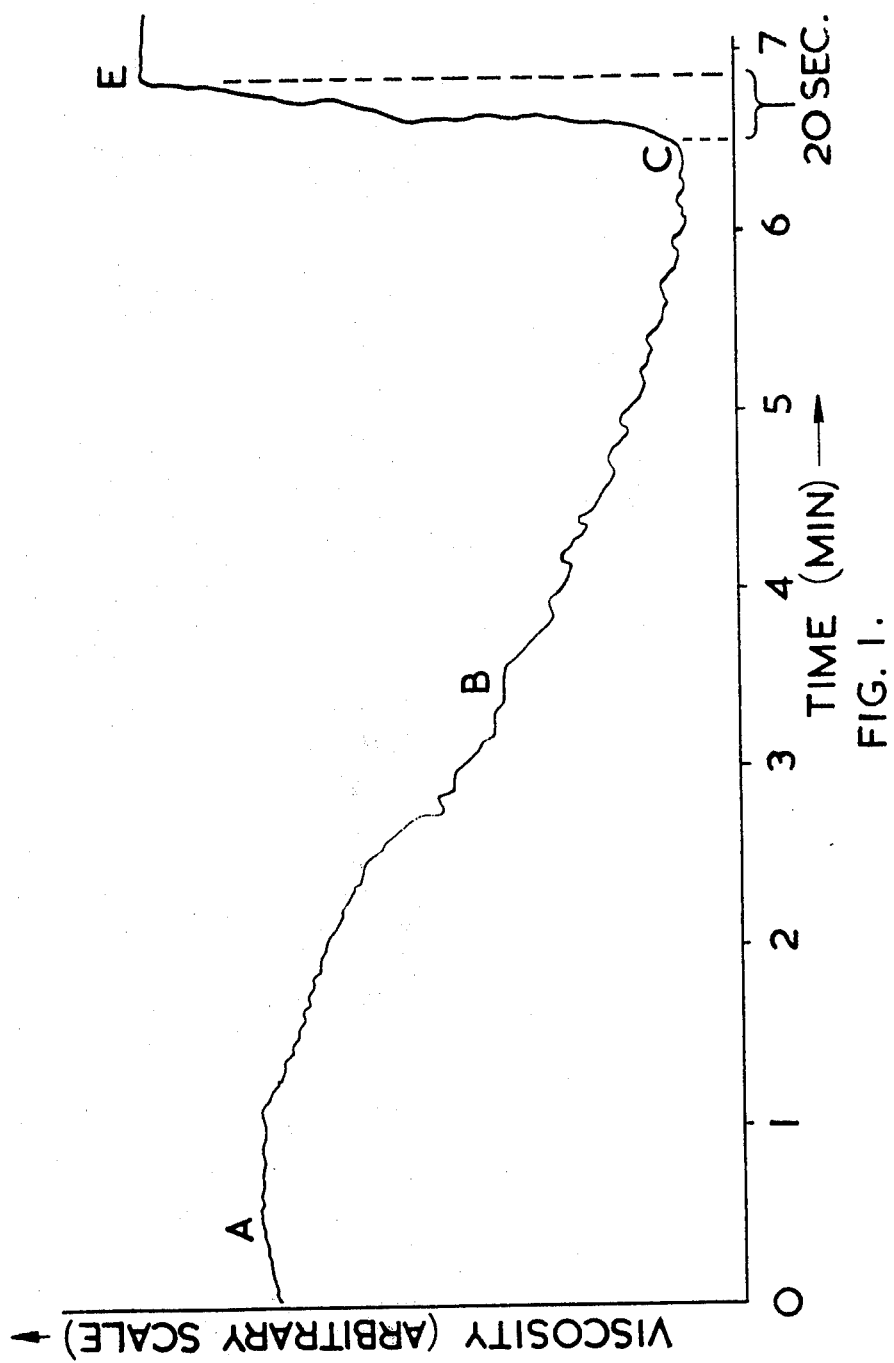
FIGS. 1, 2 and 3 illustrate typical viscosity changes of plastics materials during processing.
Figure 2:
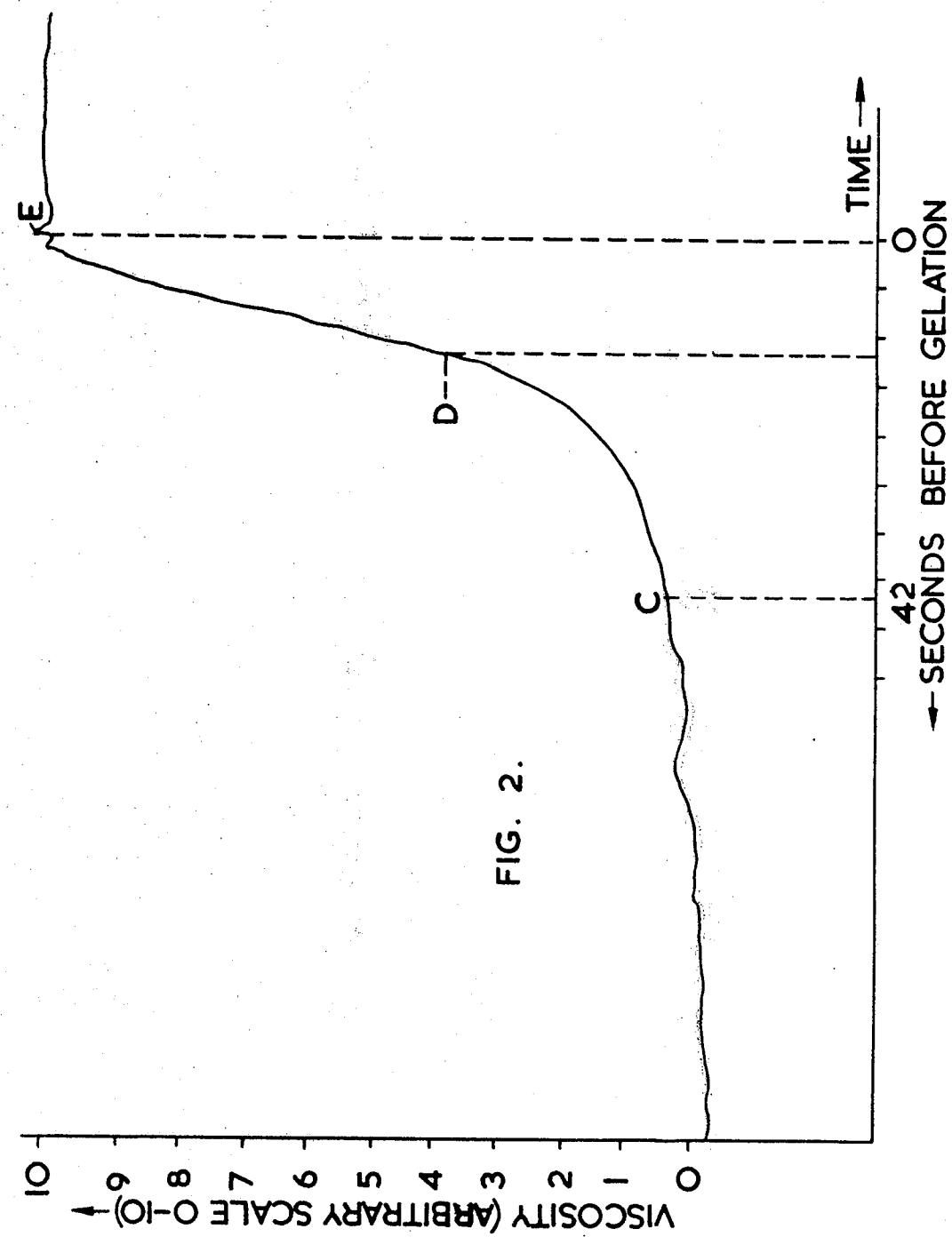
Figure 3:
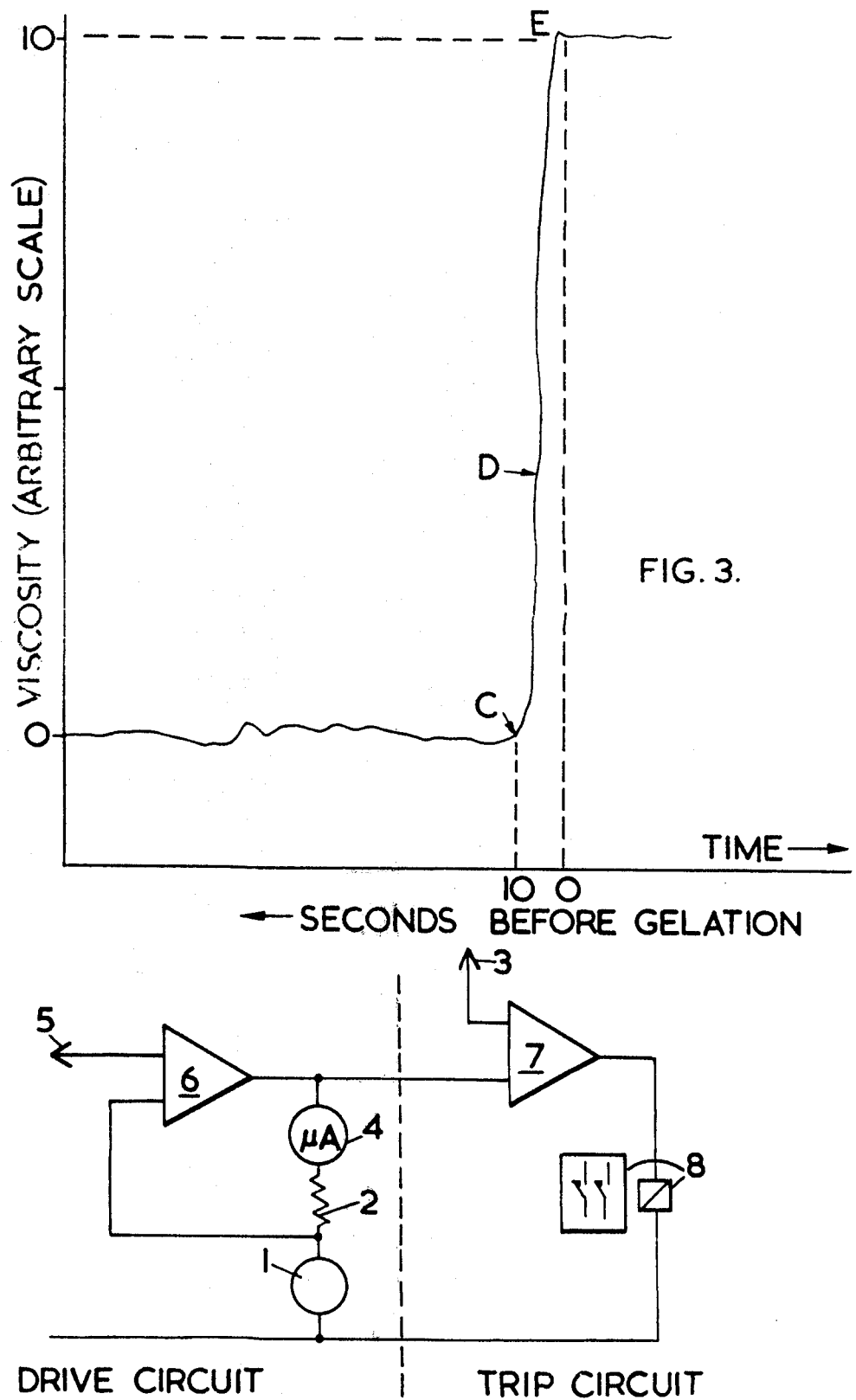

During the curing cycle, the motor current remains substantially constant until the onset of polymerisation at point C in FIGS. 1, 2 and 3 when an increase is observed. At a predetermined stage in the polymerisation as indicated by the motor current the increase in pressure applied to the mould is commenced and continues according to a predetermined pressure-time program incorporated in the press. The apparatus can be adjusted to select the stage in the gelation cycle at which the application of moulding pressure is to commence.

The pressure applied to the mould can either be applied manually or by a servomechanism (not shown) of conventional type controlled by the relay contacts 8(2).

It may be found with some systems that a progressive increase in pressure during gelation is required to give satisfactory dimensional accuracy and surface finish. The servomechanism may be arranged to operate accordingly and a second control circuit set to actuate at a higher relative viscosity may be provided.

The time between onset of polymerisation and complete gelation in FIGS. 2 and 3 can be seen to vary for the two polymers, being 42 seconds for the epoxy resin and 10 seconds for the polyester. However, the resistance set on switch 3 may be adjusted to give the same range of output between points C and E so that the relay 8 always operates at the point D.

A suitable size for the glass rod 11 is 2 mm diameter and 20 cm long and the rod may be inserted to a depth of 2 cm in the spillway 53 which is 5 or 6 mm diameter. However, other dimensions and proportions may be used. Also the viscosity of the resin at which the motor is stalled may be varied by altering the probe diameter as well as by altering the input motor voltage.

We claim

1. An apparatus for detecting a change in viscosity of a material, the change being from a highly fluid state to a high viscosity "set" state, comprising a probe, a motor for rotating said probe in a sample of the material, an operational amplifier having a negative feedback loop electrically connected to said motor, said amplifier providing current for driving said motor and said feedback loop compensating partially for the effect of increased loads on said motor, and means for measuring a parameter of the said combination, which parameter varies in accordance with the logarithm of the viscosity of said sample of material.

2. Apparatus according to claim 1 in which the motor is an ironless motor.

3. Apparatus according to claim 2 further including a constant voltage source for driving the ironless motor and wherein said measuring means includes means for measuring the current drawn by the motor, wherein the current drawn varies in accordance with the logarithm of the viscosity of said sample of material.

4. Apparatus according to claim 1 in which the probe is a disposable probe.

5. Apparatus according to claim 1 and further comprising servomechanical means for controlling a compression moulding press containing said material by which an increase in pressure is applied to the body of said material when the parameter reaches a predetermined value.

6. Apparatus according to claim 3 further comprising a current meter for measuring the current drawn by said motor, and means for calibrating said current meter.

* * * * *